United States Patent [19]

Quick

[11] 4,312,779
[45] Jan. 26, 1982

[54] RECOVERY OF CATALYSTS

[75] Inventor: Michael H. Quick, Palatine, Ill.

[73] Assignee: UOP Inc., Des Plaines, Ill.

[21] Appl. No.: 190,774

[22] Filed: Sep. 25, 1980

[51] Int. Cl.³ .................. B01J 31/40; B01J 31/20; C07C 29/16; C01G 55/00
[52] U.S. Cl. ........................... 252/411 R; 423/22; 423/143; 568/909
[58] Field of Search ............... 252/411 R; 568/909, 568/454, 455; 423/22, 417, 143; 75/108, 121

[56] References Cited

U.S. PATENT DOCUMENTS

| | | | |
|---|---|---|---|
| 2,880,241 | 3/1959 | Hughes | 260/604 |
| 3,555,098 | 1/1971 | Olivier et al. | 568/455 |
| 3,887,489 | 6/1975 | Fannin | 75/121 |
| 4,115,428 | 9/1978 | Vidal et al. | 423/417 |
| 4,247,486 | 1/1981 | Brewester et al. | 568/454 |

FOREIGN PATENT DOCUMENTS 1588014  4/1970  France ........................ 423/22

*Primary Examiner*—P. E. Konopka
*Attorney, Agent, or Firm*—James R. Hoatson, Jr.; Raymond H. Nelson; William H. Page, II

[57] ABSTRACT

Metal catalyst complexes such as those containing a metal of Group VIII of the Periodic Table which have been used in organic reactions such as the hydroformylation of olefins to form alcohols may be recovered from the product alcohols by treating said alcohol with anhydrous gaseous ammonia at temperatures in the range of from about 0° to about 100° C. and pressures in the range of from about 5 to about 1000 psi to precipitate the solution catalyst complex and thereby enable the separation of the catalyst complex from the product to be accomplished in a relatively simple manner.

11 Claims, No Drawings

RECOVERY OF CATALYSTS

DESCRIPTION OF THE INVENTION

This invention relates to a process for the recovery of metal catalyst complexes which have been used in organic reactions. More specifically, the invention is concerned with a process for recovering metal catalysts such as Group VIII metal complexes which have been utilized to synthesize alcohols in a one-step hydroformylation reaction.

Alcohols are important basic chemicals which find a wide variety of uses in industry. For example, ethyl alcohol is a basic chemical which is used as a solvent and in the manufacture of intermediates, dyes, synthetic drugs, synthetic rubbers, detergents, cleaning source, surface coatings, cosmetics, pharmaceuticals, rocket fuel, beverages, etc. Isopropyl alcohol is used in the manufacture of acetone which in turn is a source of acetic anhydride, diacetone alcohol, methyl isobutyl ketone and other derivatives. It is also used as a solvent for essential oils, gums, resins; as a latent solvent for cellulose derivatives; as an anti-stalling agent in liquid fuels or as an intermediate in the manufacture of pharmaceuticals, perfumes, lacquers, rocket fuel, etc. Likewise, dodecyl alcohol which is also known as lauryl alcohol is used in the manufacture of synthetic detergents, lube additives, pharmaceuticals, rubber, textiles, and perfumes. Tetradecanol which is also known as myristyl alcohol is used in organic synthesis, as a plasticizer, anti-foam agent, as a perfume fixative for soaps and cosmetics as well as other uses.

The prior art has shown, as exemplified by the Oxo process, that aldehydes may be produced from olefinic hydrocarbons by treatment with carbon monoxide and hydrogen using a cobalt carbonyl catalyst. It has further been shown in the prior art, as exemplified by U.S. Pat. No. 2,880,241, that rhodium is known to be a much more active catalyst than cobalt. The activity and selectivity of rhodium catalysts may be altered by modifying the catalyst with other compounds such as tertiary amines. For example, when using tertiary amines to modify rhodium catalysts, it is possible to produce alcohols rather than aldehydes in this process.

The commercialization of processes for the synthesis of alcohols utilizing rhodium complex catalysts is affected by the difficulty which is attendant in the recovery of rhodium, a particular disadvantage which negates the commercial use of such catalyst complexes comprising the frequent losses of the precious metal which may occur under process conditions, the loss of only a trace amount of this precious metal making the process uneconomical to operate and overshadowing the attractive conversion rate and selectivity which is obtained when using this metal. The separation of the rhodium catalyst from alcohol products, especially high molecular weight alcohols by conventional means such as distillation, is not practical inasmuch as the unstable rhodium-amine complex decomposes in a distillation apparatus, thus resulting in the loss of the rhodium by plating or precipitation on the surfaces of the processing equipment.

A particular advantage of utilizing a one-step synthesis of alcohol lies not only in a lower process cost and capital cost, when compared with the conventional Oxo process to produce aldehydes or alcohols, but also results in a higher yield of the desired products. This is particularly advantageous inasmuch as loss of aldehydes which easily takes place during distillation via their condensation in a still does not occur in this process.

It is therefore an object of this invention to provide a process for the recovery of metal catalyst complexes which have been used in organic reaction processes.

A further object of this invention is found in a process for the recovery of metal catalyst complexes in which the metal portion of the complex is a Group VIII metal, said catalyst having been used in various organic reactions such as hydroformylation.

In one aspect an embodiment of this invention resides in a process for the recovery of a metal catalyst complex from an organic reaction product which comprises treating said product with gaseous anhydrous ammonia at treatment conditions, separating the resultant solid metal catalyst complex from said reaction product, and recovering the metal catalyst complex.

A specific embodiment of this invention is found in a process for the recovery of rhodium from dodecanol which has been obtained from the treatment of hendecene with carbon monoxide and hydrogen at a temperature in the range of from about 50° to about 250° C. and a pressure in the range of from about 50 to about 300 atmospheres in the presence of hexarhodiumhexadecacarbonyl which comprises treating said dodecanol with gaseous anhydrous ammonia at a temperature in the range of from about 0° to about 100° C. and a pressure in the range of from about 5 to about 1000 psi, separating the resultant solid rhodium carbonyl complex from said dodecanol, and recovering the rhodium carbonyl complex.

Other objects and embodiments will be found in the following further detailed description of the present invention.

As hereinbefore set forth the present invention is concerned with a process for the recovery of metal catalyst complexes which have been utilized in various reactions such as the synthesis of alcohols by means of a hydroformylation reaction involving the treatment of olefinic hydrocarbons with carbon monoxide and hydrogen in the presence of these compounds. The recovery of the expensive catalysts is imperative from an economic and commercial standpoint and, in addition, traces of the aforesaid catalyst which may be present in the reaction product should be removed from said product in order to render the same usable for various purposes.

Various methods for recovery of catalysts from reaction products have been proposed including such methods as treating the product with aqueous ammonium hydroxide solutions to extract the catalyst, thereafter stripping ammonia from the ammonium hydroxide catalyst and treating the stripped ammonium hydroxide solution with various compounds such as amines, organic products themselves, etc., in order to recover the desired catalyst. However, these methods entail the use of relatively complicated equipment and additional process steps in order to effectively recover the catalyst. As will hereinafter be shown in greater detail, it has now been discovered that metal catalyst complexes and particularly metal catalyst complexes in which the metal is selected from Group VIII of the Periodic Table may be recovered in a relatively inexpensive and simple manner by treating an organic reaction product with gaseous anhydrous ammonia to effect the precipitation of the catalyst complex and thus enable it to be easily separated from the liquid organic product.

As an illustration of one type of organic reaction in which the catalyst which is employed may be recovered, the synthesis of an alcohol may be effected by reacting an olefinic hydrocarbon with carbon monoxide and hydrogen in the presence of a catalyst comprising a complex containing a Group VIII metal and a promoter or modifier comprising an amine compound, and preferably a tertiary amine. The reaction conditions which are employed to synthesize the alcohol will include a temperature of from about 50° to about 250° C. and a pressure in the range of from about 50 to about 300 atmospheres. In the preferred embodiment of the process the pressures which are employed to effect the desired result will be the autogenous pressures resulting from the presence of hydrogen and carbon monoxide in the reaction mixture. However, it is also contemplated within the scope of this process that the pressures resulting from the use of hydrogen and carbon monoxide will comprise only a partial operating pressure, the remainder being provided for by the introduction of a substantially inert gas such as nitrogen, helium, argon, etc., into the reaction vessel. In addition, other reaction conditions which are present during the synthesis of the alcohol will include a mole ratio of hydrogen to carbon monoxide in the range of from about 0.5:1 to about 5:1 moles of hydrogen per mole of carbon monoxide, a mole ratio of olefin to catalyst in the range of from about 500:1 to about 2000:1 moles of olefin per mole of catalyst and a mole ratio of tertiary amine modifier to catalyst in the range of from about 50:1 to about 300:1 moles of amine per mole of catalyst.

Examples of olefinic hydrocarbons which may be employed as feed stocks will include straight and branched chain olefins containing from 2 to about 30 carbon atoms such as propylene, butene-1, butene-2, isobutylene, pentene-1, pentene-2, isopentene, as well as the isomeric hexenes, heptenes, octenes, nonenes, decenes, undecenes, dodecenes, tridecenes, tetradecenes, pentadecenes, hexadecenes, heptadecenes, oxtadecenes, nonadecenes, eicosenes, heneicosenes, docosenes, tricosenes, tetracosenes, pentacosenes, hexacosenes, heptacosenes, octacosenes, nonacosenes, triacontenes, etc.; product mixtures produced by the dehydrogenation of $C_{11}$ to $C_{14}$ n-paraffins containing $C_{11}$ to $C_{14}$ n-olefins as well as unconverted $C_{11}$ to $C_{14}$ n-paraffins or olefin fractions of paraffin dehydrogenation processes; olefin fractions of cracking processes; ethylenically unsaturated compounds such as styrene, allyl alcohol, methyl vinyl ketone, and cyclohexene.

The reaction between the olefinic hydrocarbon of the type hereinbefore set forth, carbon monoxide and hydrogen is effected in the presence of a Group VIII metal complex catalyst which may be organo-metallic in nature or which may comprise a salt which is converted to the complex catalyst during the process under the reaction conditions employed. Specific examples of these Group VIII metal catalysts will include rhodium nitrate, rhodium chloride, rhodium bromide, rhodium iodide, rhodium fluoride, chlorodicarbonylrhodium dimer, chlorobis(ethylene)rhodium dimer, hexarhodiumhexadecacarbonyl, tetrarhodiumdodecacarbonyl, rhodium acetate, rhodium acetylacetonate, ruthenium nitrate, ruthenium chloride, ruthenium bromide, ruthenium iodide, ruthenium carbonyl, ruthenium acetate, chlorodicarbonylruthenium dimer, chlorobis(ethylene)ruthenium dimer, cobalt nitrate, cobalt chloride, cobalt bromide, cobalt iodide, cobalt acetate, cobalt acetylacetonate, and hexacobalthexadecacarbonyl. The modifier which is utilized to selectively form alcohols will comprise a tertiary amine, said tertiary amine including alkyl amines, aryl amines, heterocyclic amines, cycloalkyl amines, etc., such as trimethylamine, triethylamine, tripropylamine, the isomeric tributylamines, tripentylamines, trihexylamines, triheptylamines, trioctylamines, trinonylamines, tridecylamines, dimethylethylamine, dimethylpropylamine, dimethylbutylamine, dimethyldodecylamine, triphenylamine, tribenzylamine, tri-o-tolylamine, tri-m-tolylamine, tri-p-tolylamine, tricyclopentylamine, tricyclohexylamine, N-methylpyridine, N-methylpyran, N-ethylpyridine, N-ethylpyran, etc. It is to be understood that the aforementioned olefinic hydrocarbons, Group VIII metal and tertiary amines are only representative of the class of compounds which may be employed and that the present process is not necessarily limited thereto.

After synthesizing the alcohol the product is recovered, said product containing a Group VIII metal catalyst complex. In order to separate the aforesaid catalyst which is soluble in the organic reaction product, it is necessary to treat said product. In the process of the present invention the reaction product containing the catalyst is treated with gaseous anhydrous ammonia at treatment conditions, said treatment conditions including a temperature in the range of from about 0° to about 100° C. and a pressure in the range of from about 5 to about 1000 pounds per square inch (psi). If so desired, the treatment of the product with the gaseous anhydrous ammonia is effected under an inert atmosphere, said inert atmosphere being provided for by the introduction of nitrogen, helium, argon, etc., into the treatment zone. After treating the organic reaction product with the ammonia for a period of time which may range from about 0.5 up to about 10 hours or more in duration, the metal catalyst complex which precipitates out during the treatment step is separated from the liquid organic reaction product by filtration, centrifugation, decantation, or any other suitable method known in the art.

The process of this invention may be effected in any suitable manner and may comprise either a batch or continuous type operation. For example, when a batch type operation is used, the organic reaction product which has been obtained and which contains a Group VIII metal catalyst complex which is soluble in the reaction product is placed in an appropriate pressure resistant apparatus, one example of such an apparatus being an autoclave of the rotating, mixing or stirring type. The gaseous anhydrous ammonia is charged to the apparatus under an inert atmosphere such as nitrogen until the desired operating pressure has been attained. The apparatus is then heated to the desired temperature for a predetermined period of time in order to allow or insure the complete precipitation of the metal catalyst complex. At the end of the desired operating period of time, heating is discontinued, if elevated temperatures have been employed, and after the apparatus has returned to room temperature the excess pressure is discharged. The apparatus is then opened and the reaction mixture recovered therefrom followed by conventional means of separating the solid catalyst complex from the liquid reaction product.

It is also contemplated within the scope of this invention that the process described herein for the recovery of Group VIII metal catalyst complexes may be effected in a continuous manner of operation. When such a type of operation is employed the organic reaction product containing the soluble catalyst is continuously charged to a reaction zone which is maintained at the proper operating conditions of temperature and pressure. The proper operating pressure is effected by charging thereto the anhydrous ammonia along with, if so desired, an inert gas of the type hereinbefore set forth in greater detail. After passage through the reaction zone for a predetermined period of time the reactor effluent is continuously withdrawn and subjected to conventional means of separation whereby the desired organic reaction product in liquid form is separated from the solid metal catalyst complex which has precipitated out during the reaction period, the latter then being available for recycle back to the organic reaction zone for use therein as a portion of the catalyst necessary to effect the desired organic reaction.

The following examples are given for purposes of illustrating the process of this invention. However, it is to be understood that these examples are merely illustrative of the process, and that the present invention is not necessarily limited thereto.

EXAMPLE I

An olefinic charge comprising 326 grams of a blend of N-hendecene with smaller amounts of aromatic and paraffinic impurities was charged to a 3 liter rotating autoclave along with a catalyst comprising 0.304 grams [(175,000 micrograms of rhodium) of hexarhodiumhexadecacarbonyl] and 55 grams of an amine modifier comprising dimethyldodecylamine. The autoclave was sealed and 210 atmospheres of a 1:1 blend of carbon monoxide and hydrogen was charged thereto at room temperature. The autoclave was then heated to a temperature of 150° C., and maintained thereat for a period of 8 hours. At the end of the 8 hour period, heating was discontinued and after the autoclave was allowed to return to room temperature, the final pressure at this temperature being 143 atmospheres, the excess carbon monoxide and hydrogen was discharged. After venting the excess gas, 50 grams of anhydrous ammonia gas under a nitrogen atmosphere was charged to the autoclave which contained about 400 grams of reaction product comprising dodecanol until a total pressure of 20 psig was attained. The autoclave was then rotated at room temperature for a period of 1 hour, at the end of which time a yellow solution plus some yellow precipitate was obtained.

The solution was then evacuated under a pressure of 100 mm of mercury for a period of 4 hours in order to insure the complete removal of excess ammonia. It was noted that an additional amount of precipitate formed during this 4 hour period and in addition the color changed from yellow to brown. At the end of the period the mixture was filtered under a nitrogen atmosphere, the yellow filtrate was concentrated by distillation at 4 mm Hg and a temperature of 135° C. and analyzed by means of atomic absorption spectroscopy. In addition, the brown solid which remained on the filter paper was also analyzed by atomic absorption spectroscopy. This analysis determined that there was 33,000 micrograms of rhodium in the filtrate and 121,000 micrograms of rhodium in the solid. The analysis determined that a substantial amount of rhodium (69%) was precipitated by the gaseous anhydrous ammonia treatment and removed from the product, while the amount of rhodium recovered was 89% overall.

EXAMPLE II

In a manner similar to that set forth in Example I above, the treatment of reaction products such as pentanol, nonanol, or hexadecanol which have been prepared from olefinic hydrocarbons such as butene, octene or pentadecene in a hydroformylation reaction using catalysts such as chlorodicarbonylrhodium dimer, ruthenium carbonyl or hexacobalthexadecacarbonyl with gaseous anhydrous ammonia may also result in the recovery of the catalyst complex from the product alcohols.

I claim as my invention:

1. A process for the recovery of cobalt, rhodium or ruthenium metal complex catalyst from a liquid hydroformylation alcohol reaction product obtained from treatment of an olefinic hydrocarbon with hydrogen and carbon monoxide in the presence of said cobalt, rhodium or ruthenium metal complex catalyst at hydroformylation conditions comprising a temperature in the range of from about 50° to about 250° C. and a pressure in the range of from about 50 to about 300 atmospheres, which recovery process comprises treating said hydroformylation alcohol reaction product with an effective amount of gaseous anhydrous ammonia at a temperature in the range of from about 0° to about 100° C. and a pressure in the range of from about 5 to about 1000 p.s.i. to precipitate said cobalt, rhodium or ruthenium metal complex catalyst, separating said precipitated cobalt, rhodium or ruthenium solid metal complex catalyst precipitate from said hydroformylation alcohol reaction product, and recovering said cobalt, rhodium or ruthenium solid metal complex catalyst.

2. The process as set forth in claim 1 further characterized in that said gaseous anhydrous ammonia treatment is effected in an inert atmosphere.

3. The process as set forth in claim 2 in which said inert atmosphere is supplied by the presence of nitrogen.

4. The process as set forth in claim 1 in which said rhodium metal catalyst complex comprises hexarhodiumhexadecacarbonyl.

5. The process as set forth in claim 1 in which said rhodium metal catalyst complex comprises chlorodicarbonylrhodium dimer.

6. The process as set forth in claim 1 in which said ruthenium metal catalyst complex comprises ruthenium carbonyl.

7. The process as set forth in claim 1 in which said cobalt metal catalyst complex comprises hexacobalthexadecacarbonyl.

8. The process as set forth in claim 1 in which said alcohol is dodecanol and said olefinic hydrocarbon is hendecene.

9. The process as set forth in claim 1 in which said alcohol is pentanol and said olefinic hydrocarbon is butene.

10. The process as set forth in claim 1 in which said alcohol is nonanol and said olefinic hydrocarbon is octene.

11. The process as set forth in claim 1 in which said alcohol is hexadecanol and said olefinic hydrocarbon is pentadecene.

* * * * *